Figures 1A, 1B, 1C, 1D:
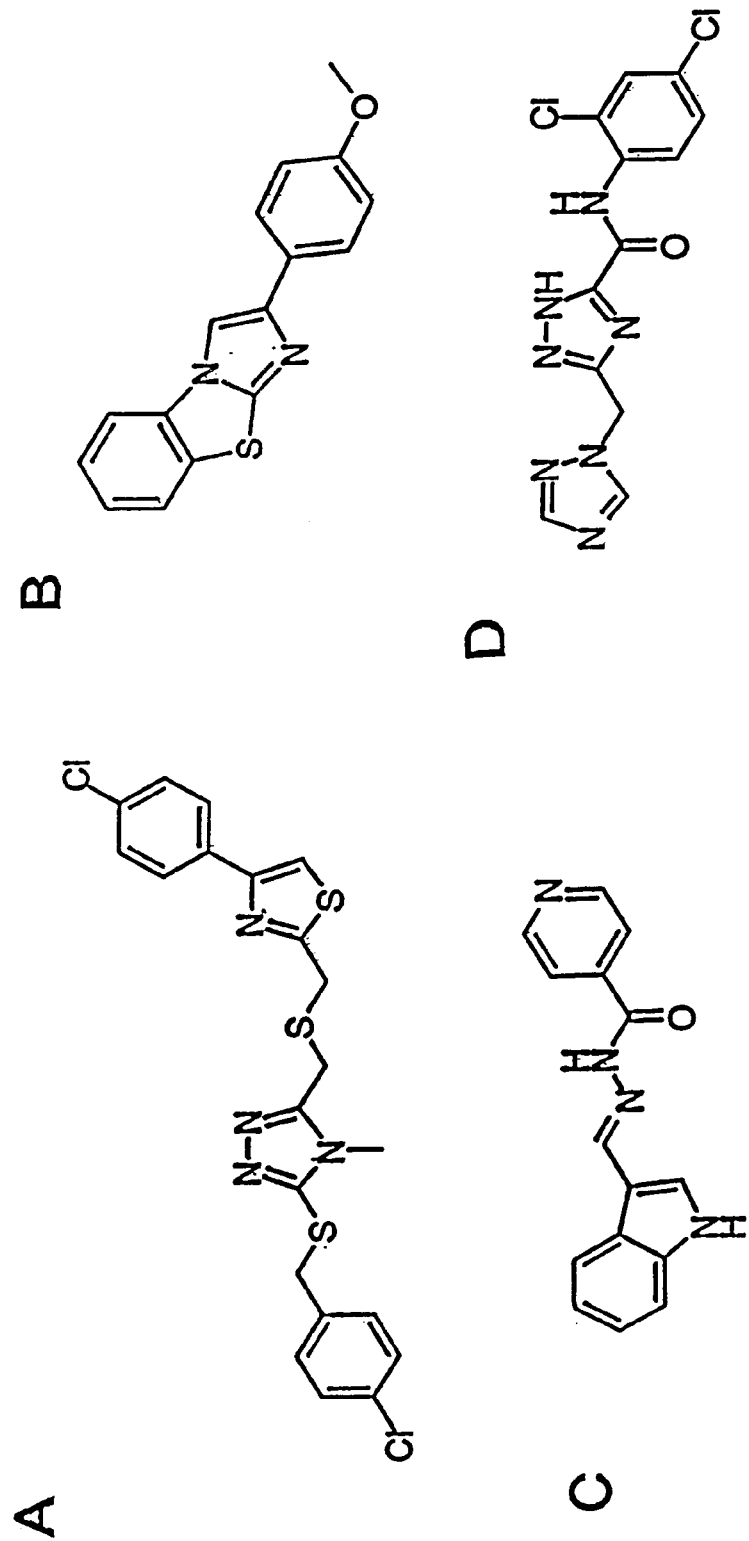

United States Patent [19]
Huang et al.

[11] Patent Number: 6,127,387
[45] Date of Patent: Oct. 3, 2000

[54] USE OF CD4-BINDING SMALL MOLECULES TO INHIBIT IMMUNE RESPONSES

[75] Inventors: Ziwei Huang, Philadelphia, Pa.; Robert Korngold, Cherry Hill, N.J.

[73] Assignee: Thomas Jefferson University, Philadelphia, Pa.

[21] Appl. No.: 08/987,086

[22] Filed: Dec. 9, 1997

Related U.S. Application Data

[60] Provisional application No. 60/032,996, Dec. 10, 1996.

[51] Int. Cl.[7] ................................................. A61K 31/425
[52] U.S. Cl. ........................ 514/330; 514/339; 514/355; 514/366; 514/383; 514/825; 514/885; 514/903
[58] Field of Search ................................... 514/330, 355, 514/339, 366, 383, 825, 885, 903

[56] References Cited

U.S. PATENT DOCUMENTS

| | | | |
|---|---|---|---|
| 4,497,817 | 2/1985 | Murase et al. | 548/150 |
| 4,882,336 | 11/1989 | Tigyi et al. | 514/283 |

FOREIGN PATENT DOCUMENTS

WO 94/11014   5/1994   WIPO .

OTHER PUBLICATIONS

Acha–Orbea et al., 1988, Cell 54:263–273.
Anderson et al., 1987, J. Immunol. 139:678–682.
Barber et al., 1989, Proc. Natl. Acad. Sci. 86:3277–3281.
Ben–Nun et al., 1981, Eur. J. Immunol. 11:195–199.
Bernard et al., 1975, J. Immunol. 114:1537–1540.
Chou et al., 1983, J. Immunol. 130:2183–2186.
Clayton et al., 1989, Nature 339:540–51.
Davis et al., 1990, J. Biol. Chem. 265:10410–10418.
Dianzani et al., 1990, Eur. J. Immunol. 20:2249–2257.
Doyle et al., 1987, Nature 330:256–259.
Emmrich et al., 1987, Eur. J. Immunol. 17:529–534.
Gay et al., 1987, Nature 328:626–629.
Hafler et al., 1988, J. Immunol. 141:131–138.
Hafler et al., 1989, Immunology Today 10:104–107.
Jameson et al., 1994, Nature 368:744–746.
Janeway 1991, Seminars in Immunology 3:153–160.
June et al., 1990, J. Immunol. 144:1591–1599.
Korngold et al, 1986, Immunogenetics 24:309–315.
Kuchroo et al., 1992, J. Immunol. 148:3776–3782.
Langedijik et al., 1993, J. Biol. Chem. 268:16875–16868.
Lee et al., 1971, J. Mol. Biol. 55:379–400.
Lindsly et al., 1994, Annals of Neurology 36:183–189.
MacRae et al., 1995, J. Neuroimmunol. 60:17–28.
Martin et al., 1992, Ann. Rev. Immunol. 10:153–187.
Meng et al, 1992, J. Comput. Chem. 13:505–525.
Miceli et al., 1993, adv. Immunol. 53:59–121.
Moebius et al., 1992, Proc. Natl. Acad. Sci. 89:12008–12012.
Moebius et al., 1993, Proc. Natl. Acad. Sci. 90:8259–8263.
Mosier et al., 1988, Nature 335;256–259.
Peters et al., 1996, J. Mol. Biol. 256:201–213.
Pettineli et al., 1981, J. Immunol. 127:1420–1421.
Racadot et al., 1993, J. Autoimmunity 6:771–786.
Raine et al., 1991, Neuropath. appl. Neurobiol. 17:265–274.
Raine et al., 1988, J. Neuroimmunol. 20:189–201.
Ring et al., 1993, Proc. Natl. Acad. Sci, 90:3583–3587.
Rivas, 1988, J. Immunol. 140:2912–2918.
Saizawa et al., 1987, Nature 328:260–263.
Sakihama et al, 1995, Proc. Natl. Acad. Sci. 92:6444–6448.
Satoh et al, 1996, Biochem. Biophys. Res. Com. 224:438–443.
Steinman et al., 1993, Proc. Natl. Acad. Sci. USA 78:7111–7114.
Teh, et al., 1991, Nature 349:241–243.
Traugott et al., 1985, Cellular Immunology 91:240–254.
Turner et al., 1990, Cell 60:755–765.
Veillette et al., 1988, Cell 55:301–308.
Waldor et al, 1985, Science 227:415–417.
Weber et al., 1993, Int. Immunol. 5:695–698.
White et al., 1978, J. Exp. Med. 148:664–673.
Wraith et al., 1989, Cell 59:247–255.
Zhang et al., 1996, Nature Biotechnology, 14:472–475.

*Primary Examiner*—Frederick Krass
*Attorney, Agent, or Firm*—Akin, Gump, Strauss, Hauer & Feld, L.L.P.

[57] ABSTRACT

The application concerns a method of identifying compounds that can be used to inhibit undesired human CD4[+] T cell immune responses by identifying compounds that block the interaction of CD4 and class II MHC gene products and a method of treatment which comprises administering such an identified compound. The compounds that inhibit undesired human CD4[+] T cell immune responses can be used to treat disease such as multiple sclerosis and to prevent graft rejection and graft versus host disease. More specifically, the application concerns compounds having molecular weights between about 500 and 150 that bind to the GFCC'C" portion of the D1 domain of human CD4 lymphocyte cell surface antigen.

27 Claims, 7 Drawing Sheets

USE OF CD4-BINDING SMALL MOLECULES TO INHIBIT IMMUNE RESPONSES

CROSS-REFERENCE TO RELATED APPLICATIONS

This application is entitled to priority pursuant to 35 U.S.C. § 119 (e) to U.S. Provisional Patent Application No. 60/032,996, which was filed on Dec. 10, 1996.

FIELD OF THE INVENTION

The present invention concerns the suppression of immune responses caused by the activation of T cells. More particularly, it concerns compounds that bind to a surface pocket of the D1 domain of the CD4 protein formed by the GFCC' C" sheet and the FG, CC', C' C" loops, thereby interfering with the interaction of the CD4 and class II MHC gene products. The invention further concerns methods of identifying and using such compounds to suppress undesired immune responses.

BACKGROUND OF THE INVENTION

A T cell is a type of lymphocyte, or "white blood cell", that mediates the cellular immune response to foreign macromolecules, termed antigens. While T cells are necessary for normal mammalian immune responses, in some instances it is desirable to inhibit their activation: for example, in some autoimmune diseases, the T cells of a subject respond to "self-antigens", i.e., macromolecules produced by the subject, rather than foreign-made macromolecules, and damage the cells and tissues of the subject.

Autoimmune T cell responses are found in subjects having systemic lupus erythematosus (SLE), rheumatoid arthritis (RA), insulin-dependent diabetes and multiple sclerosis (MS) and contribute to the pathophysiology of each.

T cells also cause graft rejection and graft-versus-host disease (GVHD). Graft rejection is caused by an immune response against the transplanted tissues (the graft), which are recognized as "foreign" by T cells of the recipient (host). Graft-versus-host disease is caused by engrafted T cells, which recognize host-made macromolecules as "foreign."

A. Role of CD4 in T Cell Activation

The CD4 molecule, a member of the immunoglobulin super-family, is a glycoprotein expressed on the surface of helper T cells, White, R. H. H., et al., 1978, J. Exp. Med. 148:664–73, which are one of the two major types of T cells. Helper T cells recognize antigens only when the antigens are associated with the class II products of the Major Histocompatibility Complex (class II MHC). CD4 and the T cell antigen receptor are involved in a signal transduction pathway whereby the presence of an antigen leads to the activation of an antigen-specific helper T cell. CD4 is involved in the antigen-free, intra-thymic selection of the T cell repertoire. Teh, H. S., et al., 1991, Nature 349:241–43.

The CD4 molecule has two critical functions. First, as a co-receptor with the T cell antigen receptor, CD4 binds to a non-polymorphic region of the β-chain of the class II MHC molecule on the antigen-presenting cell. Doyle, C. & Strominger, J. L., 1987, Nature 330:256–59; Gay, D., et al., 1987, Nature 328:626–29; Konig, R., et al., 1995, Nature 365:796–98. CD4 can potentiate the T cell response as much as 300 fold above the level obtained without CD4. Janeway, C. A., 1991, Seminars in Immunology 3:153–160. Second, extensive evidence suggests that CD4 is a signal transduction molecule. Studies have shown: that the cytoplasmic tail of CD4 is associated with the tyrosine kinase $p56^{lck}$, Veillette, A., et al., 1988, Cell 55:301–08; Barber, E. K., et al. 1989, Proc. Natl. Acad. Sci. 86:3277–81; Turner, J. M., et al., 1990, Cell 60:755–65; that stimulation of CD4 with an anti-CD4 monoclonal antibody increases the activity of the $p56^{lck}$ kinase, Veillette, A., et al., 1989, Nature 335:257–9; and that cross-linking of CD4 and the T cell antigen receptor enhances both T cell antigen receptor-mediated tyrosine phosphorylation, June, C. H., et al., 1990, J. Immunol. 144:1591, and lymphokine production, Anderson, P., et al., 1987, J. Immunol. 139:678–82; Emmrich, F., et al., 1987, Eur. J. Immunol. 17:529–34. These studies imply that CD4 molecules interact with the other cell-surface molecules of the T cell antigen receptor complex during the transduction of signals leading to the activation of the cell, Miceli, M. C. & Parnes, J. R., 1993, Adv. Immunol. 53:59–122: e.g., with the T cell antigen receptor/CD3 complex, Saizawa, K., et al., 1987, Nature 328:260–63; Rivas, A., 1988, J. Immunol. 140:2912–18; and with the CD45 tyrosine phosphatase, Dianzani, U., et al., 1990 Eur. J. Immunol. 20:2249–57. There have been CD4—CD4 interactions observed between solubilized CD4 proteins, Davis, S. J., et al., 1990, J. Biol. Chem. 265:10410. The binding constant of the CD4/MHC, class II, interaction is estimated to be greater than $10^{-4}$M. Weber, S., & Karjalainen, K., 1993, Int. Immunol. 5:695.

Recently, it has been suggested that oligomerization of CD4 on the cell surface may be required for stable binding to class II MHC and T-cell activation. Sakihama, T., et al., 1995, Proc. Natl. Acad. Sci. 92:6444. If there is an interaction between membrane bound CD4 proteins, molecular modeling data is consistent with the participation in the interaction of the CDR3 and C–C' loops of the D1 domains of the CD4 proteins, Langedijik, J. P. M., et al., 1993, J. Biol. Chem. 268:16875–78. The external domains (D1–D4) of the CD4 molecule are involved in these protein-protein interactions.

The studies of the interaction of CD4 and MHC, class II, gene products have been performed to determine whether mutations at selected residues of CD4 block the binding of CD4 transfected cells and MHC, class II, bearing cells. These studies suggest that the interaction involves large areas of the CD4 molecule, in particular most of the lateral surfaces of the D1 domain and the upper part of the D2 domain. Clayton, L. K. et al., 1989, Nature 339:548–51; Moebius, U. et al., 1992, Proc. Natl. Acad. Sci. 89:12008–12; Moebius, U., et al., 1993, Proc. Natl. Acad. Sci. 90:8259–63.

The apposition of the CD4 tyrosine kinase $p56^{lck}$, the T cell antigen receptor tyrosine kinase $p59^{fyn}$, and the CD45 tyrosine phosphatase, then leads to the signals that activate the T cell. Veillette, A., et al., 1988, Cell 55:301–08; Barber, E. K., et al. 1989, Proc. Natl. Acad. Sci. 86:3277–81.

B. Multiple Sclerosis Is Mediated by $CD4^+$ T cells

Pathologically, the lesions of MS consist of perivascular inflammatory cuffs in the white matter of the central nervous system. These contain activated and non-activated lymphocytes, plasma cells, monocytes, and macrophages. The majority of the small lymphocytes found in early lesions are of the helper-type, $CD4^+$ T cell subset. Raine, C. S., et al., 1988, J. Neuroimmunol. 20:189–201; Raine, C. S., 1991, Neuropath. Appl. Neurobiol. 17:265–274.

An animal model useful for the study of the treatment of human MS is experimental allergic encephalomyelitis (EAE). EAE is an experimentally induced disease that shares many of the same clinical and pathological symptoms of MS, Martin, R., et al., 1992, Ann. Rev. Immunol. 10:153–187; Hafler, D. A., et al., 1989, Immunology Today 10:104–107. Several studies in rodents have shown that, similar to MS, CD4+ T cells participate in the pathophysiology of EAE, Traugott, U., et al., 1985, Cellular Immunology 91:240–254; Ben-Nun, A., et al., 1981, Eur. J. Immunol. 11:195–199; Pettineli, R. B., et al., 1981, J. Immunol. 127:1420–1423. EAE can be induced in certain strains of mice by immunization with myelin in an adjuvant. The immunization activates CD4+ T cells specific for myelin basic protein (MBP) and proteolipid (PLP), Bernard, C. C. A., et al., 1975, J. Immunol. 114:1537–1540; Chou, C. H., et al., 1983, J. Immunol. 130:2183–2186; Kurchroo, V. K., et al., 1992, J. Immunol. 148:3776–3782. The activated T cells enter the central nervous system and their local action causes both the anatomic pathology and clinical signs, e.g., ascending hind limb paresis leading to paralysis, of the disease.

Since autoreactive CD4+ T cells have an important role in mediating the pathogenesis of MS, one approach to treating the disease is inhibiting the activation of autoreactive, CD4+ T cells. One can use for this purpose monoclonal antibodies (mAbs) to class II MHC, Steinman, L., et al., 1993, Proc. Natl. Acad. Sci. USA 78:7111–7114, or to the T cell antigen receptor, Acha-Orbea, H., et al., 1988, Cell 54:263–273. One can also competitively inhibit antigen binding to class II MHC with non-immunogenic peptides, Wraith, D. C., et al., 1989, Cell 59:247–255.

Anti-CD4 mAbs have also been shown to inhibit the development of the disease in EAE, Waldor, M. K., et al., 1985, Science 227:415–17, and several human clinical trials are currently in progress to test this approach in MS, Hafler, D. A., et al., 1988, J. Immunol. 141:131–138; Racadot, E. et al., 1993, J. Autoimmunity 6:771–786; Lindsly, J. W., et al., 1994, Annals of Neurology 36:183–189.

C. Inhibition of Immune Responses By CD4-Derived Peptides

Synthetic peptides that mimic the surface of the CD4 molecule have been used to block the function of the CD4 protein. For example, peptides, the sequence of which is derived from the sequence of the CDR3 loop of the mouse CD4 molecule have been shown to inhibit T cell activation, in vitro, and also to ameliorate murine EAE, Jameson, B. A., et al., 1994, Nature 368:744–746. These experiments have established that: (i) treatment using a CDR3-derived peptide inhibits the autoreactive T cells but not normal immune responses; (ii) treatment using a CDR3-derived peptide does not cause pan-CD4+ T cell-depletion, a peptide specific immune response, or toxic side effects, so that the chronic use of such peptides is feasible; and (iii) treatment using a CD4-derived peptide inhibits secondary T cell responses, which would likely be involved in a clinical relapse of disease, Jameson, B. A., et al., 1994, Nature 368: 744–746; W 094/11014 to Jameson, B. A., et al. The peptides used in the Jameson studies contained a 9-amino acid sequence derived from residues 86–94 of CD4 and a amino acid linker to cyclize the peptide.

WO94/11014 by B. A. Jameson et al., published May 26, 1994, discloses that peptides having sequences derived from the sequence of residues 17–22, 117–128, 130–138, and 158–171 of CD4, and subregions thereof, may also be used to modulate an immune response. Additional peptides are disclosed in U.S. patent application Ser. No. 08/368,280 by R. Korngold and B. A. Jameson, filed Jan. 3, 1995.

Zhang, X., et al., 1996, Nature Biotechnology, 14:472–475 discloses a peptide having a molecular weight of about 1500 daltons and containing residues 82–89 of CD4. The peptide of Zhang et al. is alleged to inhibit the interaction of CD4 and class II MHC as shown by blockage of antigen induced IL-2 secretion.

III. SUMMARY OF THE INVENTION

The present invention encompasses a method of inhibiting an undesired CD4 T cell immune response in a subject by administering an effective amount of a compound that blocks the interaction of CD4 and class II MHC of between 500 and about 150 daltons and preferably between 500 and 250 daltons. Compounds that inhibit CD4/class II MHC, interaction can be identified by their ability to block the rosetting of the human B-cells tumor line, Raji, around a cell that expresses CD4, but have no toxic effects, e.g., no effects on the proliferation of transformed cells. The method comprises administering a therapeutically effective amount of a compound that inhibits CD4 oligomer formation, which compound has a molecular weight of between 500 daltons and 100 daltons, preferably between 500 daltons and 250 daltons.

The present invention is further directed towards examples of such compounds, such as the organic compounds 5-(4-chlorobenzylthio)-3-{[(4-chlorophenyl)-2-thiazolyl]methylthiomethyl}-4-methyl-1,2,4-triazole; 4-(4-methoxy-phenyl)-1-[imidazo(2,1-B)benzothiazole; N-(3-indoylmethylene)-isonicotinic hydrazone; and N-(2,4-dichlorophenyl)-3-(1,2,4-triazol-1-ylmethyl)-1,2,4-triazole-5-carboxamide, that inhibit T cell activation and towards the method of using such compounds to inhibit human CD4-dependent immune responses. The invention encompasses inhibiting T cell activation by contacting T cells with an effective amount of a compound that binds to a surface pocket of the D1 domain of the CD4 protein formed by the GFCC'C" sheet and the FG, CC', C'C" loops. Further the invention encompasses methods of treating autoimmune diseases in humans, that are ameliorated by interfering with the function of the CD4 molecule.

IV. BRIEF DESCRIPTION OF THE FIGURES

FIG. 1A–1D. Four non-peptidic organic inhibitors of stable CD4-MHC class II interactions: A) TJU101, 5-(4-chlorobenzylthio)-3-{[(4-chlorophenyl)-2-thiazolyl] methylthiomethyl}-4-methyl-1,2,4-triazole; B) TJU102, 4-(4-methoxy-phenyl)-1-[imidazo(2,1-B)benzothiazole; C) TJU103, N-(3-indoylmethylene)-isonicotinic hydrazone; and D) TJU104, N-(2,4-dichlorophenyl)-3-(1,2,4-triazol-1-ylmethyl)-1,2,4-triazole-5-carboxamide.

Figure 2:
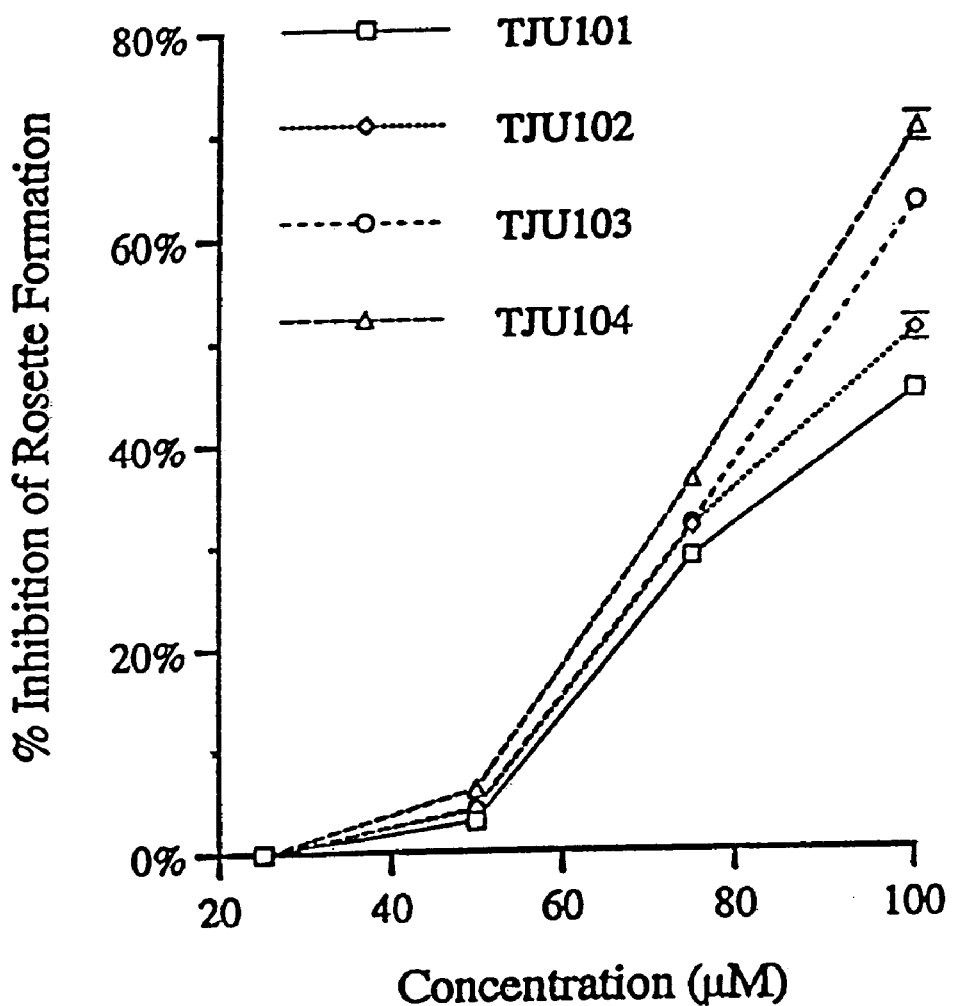

FIG. 2. Inhibitory activity by the four selected organic compounds on CD4-MHC class II binding, as measured by the cell adhesion assay. The chemical structures of these compounds are given in FIGS. 1A–1D. The points represent the mean of three independent assays.

Figure 3:
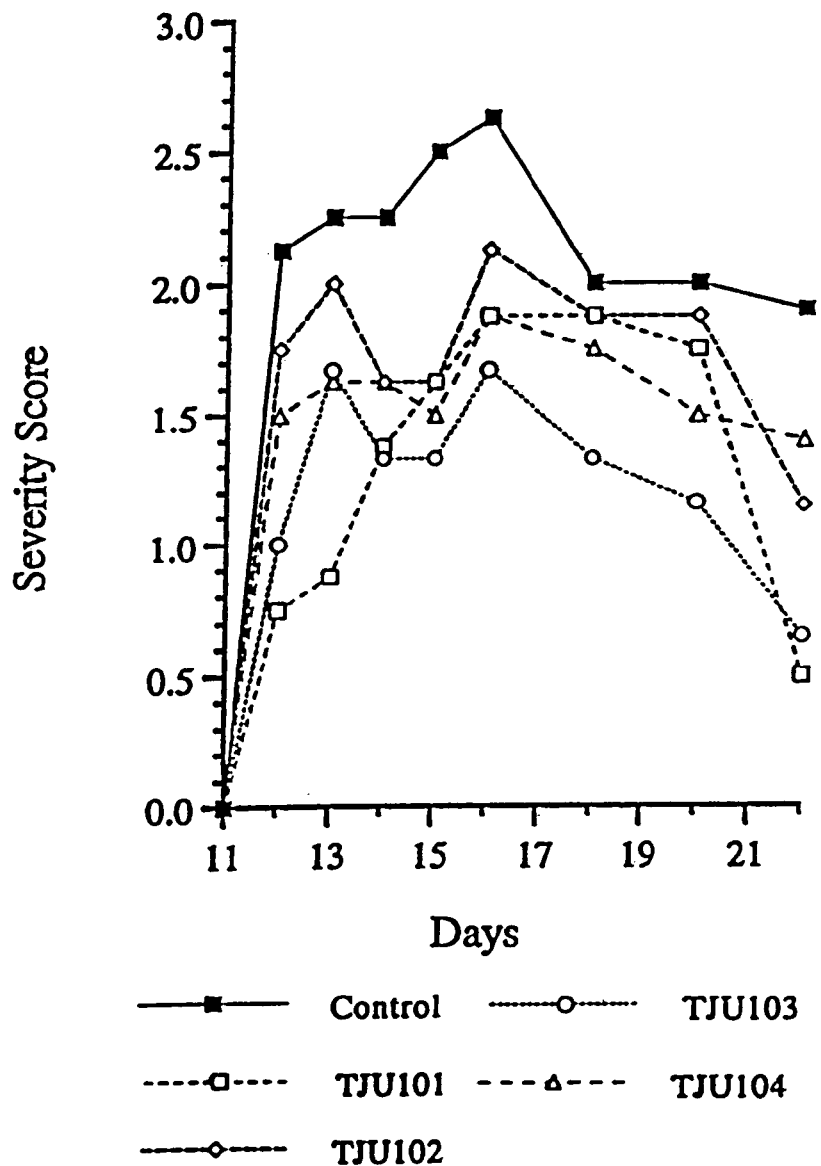

FIG. 3. Efficacy of TJU101–104 as inhibitors of the development of EAE severity in SJL/J mice.

Figure 4:
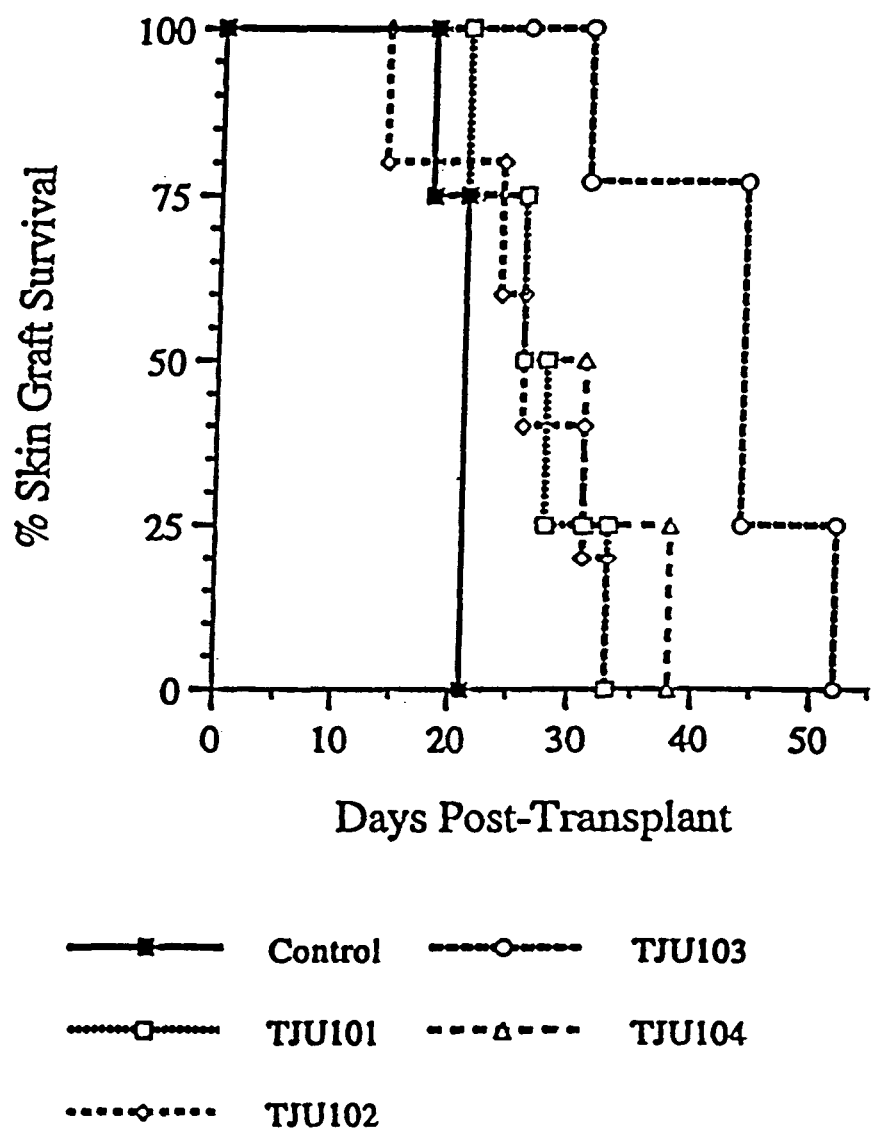

FIG. 4. Efficacy of TJU101–104 as inhibitors of allograft skin rejection in an class II MHC disparate allograft.

Figure 5:
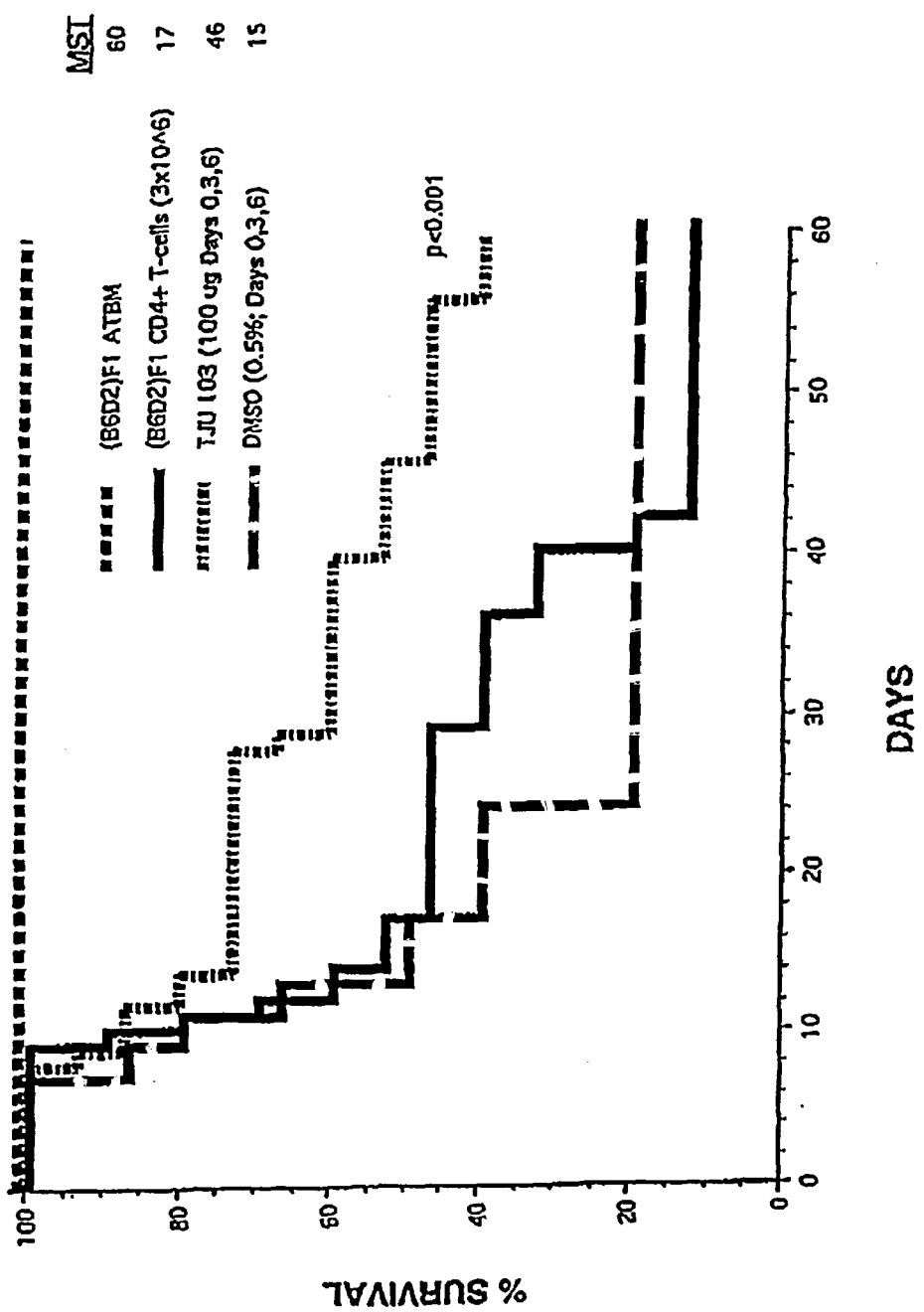

FIG. 5. Efficacy of TJU103 as inhibitor of the development of graft-versus-host disease in (B6×CBA)F$_1$ irradiated mice transplanted with haploidentical (B6×DBA/2)F$_1$ T cell-depleted bone marrow and CD4+ T cells.

Figure 6:
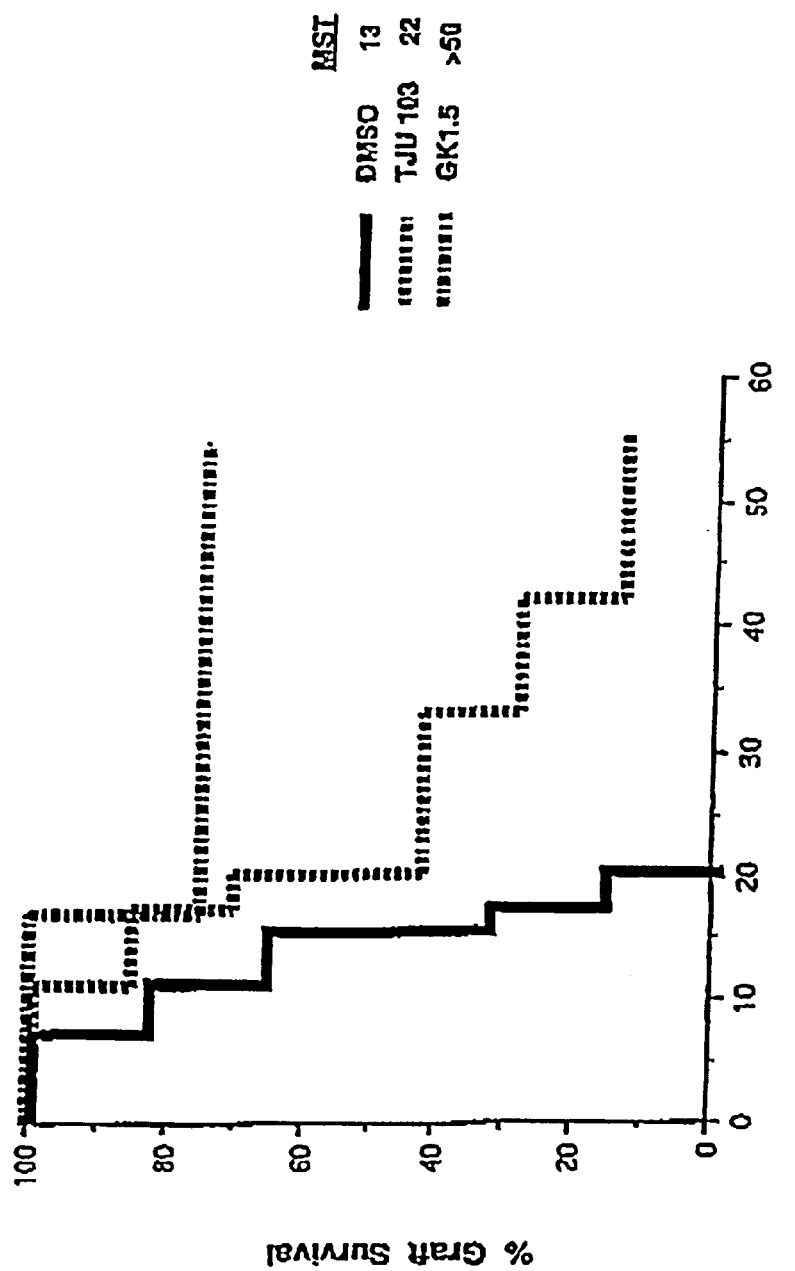

FIG. 6. Efficacy of TJU103 as inhibitor of allograft skin rejection in the CD4+ T cell-mediated B6 anti-bm12 response.

Figure 7:
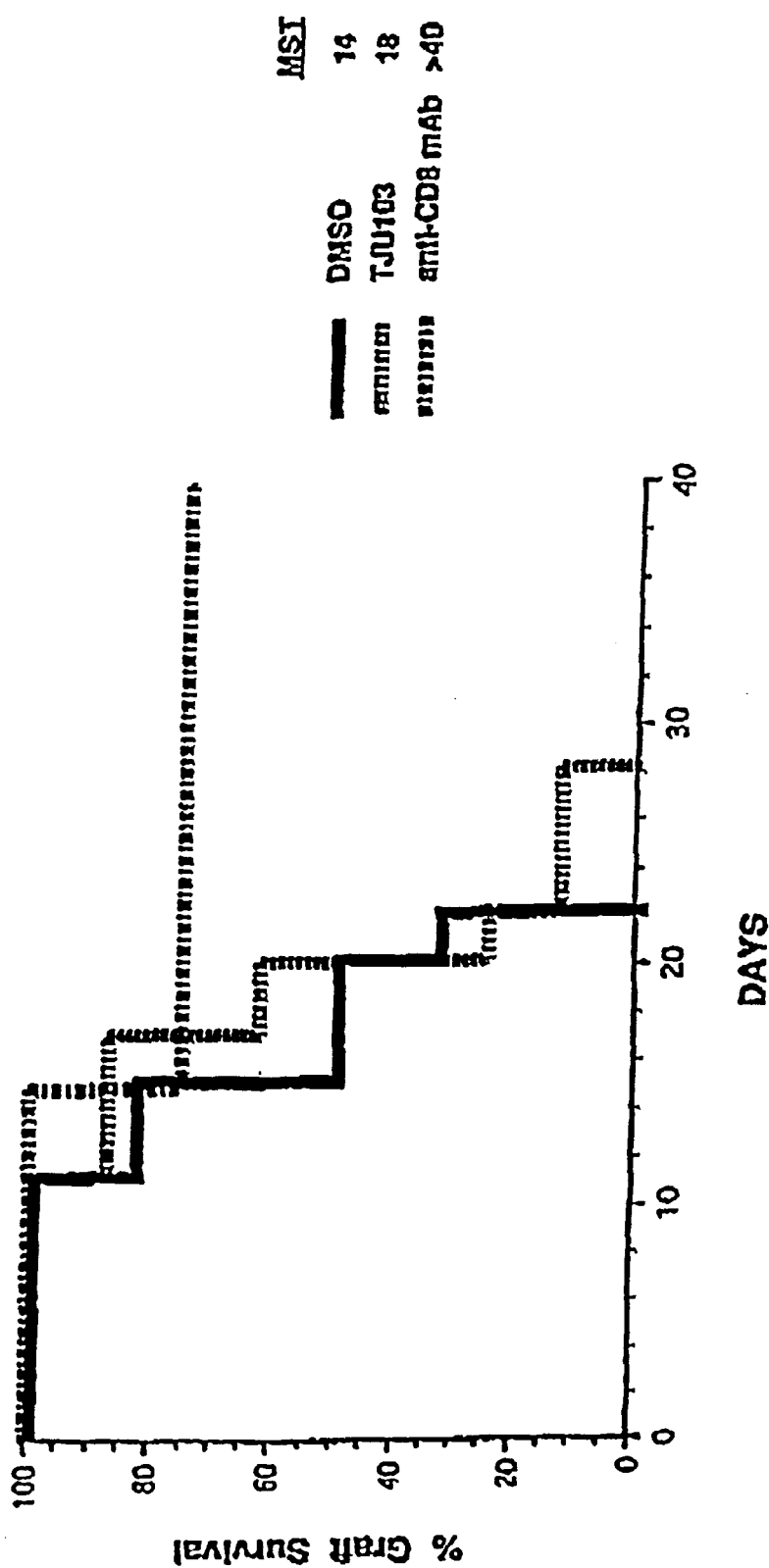

FIG. 7. Efficacy of TJU103 as inhibitor of allograft skin rejection in the CD8+ T cell-mediated B6 anti-bm1 response.

V. DETAILED DESCRIPTION OF THE INVENTION

The present invention concerns methods of inhibiting human, CD4 T-cell immune responses by administering an effective amount of a compound, the molecular weight of which is between 500 and about 150 daltons, and preferably between 500 and 250 daltons, that specifically blocks the interaction of CD4 and class II MHC, gene products. The use of compounds having higher molecular weights is subject to disadvantages in achieving and maintaining a therapeutical effective concentration. In particular embodiments of the invention, the compound is a member of the group consisting of 5-(4-chlorobenzylthio)-3-{[(4-chlorophenyl)-2-thiazolyl]methylthiomethyl}-4-methyl-1,2,4-triazole; 4-(4-methoxy-phenyl)-1-[imidazo(2,1-B) benzothiazole; N-(3-indoylmethylene)-isonicotinic hydrazone; and N-(2,4-dichlorophenyl)-3-(1,2,4-triazol-1-ylmethyl)-1,2,4-triazole-5-carboxamide.

A. METHODS OF IDENTIFYING INHIBITORS OF CD4/CLASS II MHC INTERACTION

A synthetic peptide mapping approach was employed to identify potential surface binding epitopes of the CD4 protein. As described in detail in Satoh, T., et al., 1996, Biochem. Biophys. Res. Corn. 224:438–443, which is hereby incorporated by reference, this strategy consisted of two steps. In the first step, theoretical analyses using surface binding site searching algorithms of APROPOS, Peters, K. P., et al., 1996, J. Mol. Biol. 256:201, and DOCK, Meng, E. C., et al., 1992, J. Comput. Chem. 13:505, and solvent-accessible surface area calculations, Lee, B. & Richards, F. M., 1971, J. Mol. Biol. 55:379, were carried out for the CD4 D1 domain to identify surface structural features that might mediate protein-protein interactions. Other computational methods such as Delphi, Gilson, M. K., et al., 1988, J. Comput. Chem. 9:327, were also used to analyze the electrostatic properties of CD4 surface structures. Informed by these calculations we selected an area bounded by the three loops termed: FG, residues 86–89; CC', residues 29–35; and C'C'', residues 40–43. In our model, the amino acids that form the binding site and are available to interact with an inhibitory ligand include:

$Gln^{25}$, $His^{27}$, $Glu^{85}$, $Glu^{87}$, $Asp^{88}$, $Gln^{89}$, and $Lys^{90}$.

The Available Chemicals Directory (Molecular Design Limited, San Leandro, Calif.), which is hereby incorporated by reference, was chosen as the small molecular database to be screened for potential ligands because it included approximately 150,000 commercially available small organic compounds. The structures of the molecules were generated using a heuristic algorithm, CONCORD, developed by R. Pearlman at the University of Texas.

DOCK3.5 is an automatic algorithm to screen small-molecule databases for ligands that could bind to a given receptor. Meng, E. C., et al., 1992, J. Comp. Chem. 15:505. DOCK3.5 characterizes the surface of the active site to be filled with sets of overlapping spheres. The generated sphere centers constitute an irregular grid that is matched to the atomic centers of the potential ligands. The quality of the fit of the ligand to the site is judged by either the shape complementarity or by a simplified estimated interaction energy. The 1000 molecules with the best shape complementarity scores and the 1000 with the best force field scores were selected from a DOCK3.5 screening. The resulting 2000 compounds were then visually screened thrice independently in the context of the CD4 D1 surface binding pocket using the molecular display software Insight II (Biosym Inc., San Diego, Calif.). A set of diverse compounds that possessed distinctive chemical structures, receptor binding modes, and electrostatic and shape complementarity was selected for further testing. Ultimately, 41 compounds were chosen for testing in the CD4-MHC class II cell adhesion assay. Of these 41 compounds, 37 were from the shape list, 15 were from the force-field list, and 11 appeared on both lists.

The capacity of a compound to inhibit the interaction of CD4 and class II MHC gene products can be determined by a cell rosetting assay. A cell line, such as Cos-7, Cos-1 or the like, can be transiently transfected with a plasmid bearing a human CD4 cDNA operably linked to a promoter. In an alternative embodiment a COS-1 cell line can be stably transformed with a human CD4 expression plasmid. The human CD4expressing cells and a human class II MHC expressing cell are mixed so that cellular rosettes are formed.

Specific blockage by a compound is evidenced by a reduction in the number of rosettes by at least 40% when the compound is present in the resetting medium at a concentration of at most 100 $\mu$M, and the 40% rosette-inhibitory concentration shows a less than 20% inhibition of the proliferation of transformed cells lines, e.g., EBV-transformed B-lymphoblastoid cell lines or IL-2-dependent T-cell lines, such as HT-2. No inhibition of resetting was observed when CD8-pcDNA3 transfected cells were rosetted with Raji cells, which also express MHC, class I products.

Alternatively, the activity of a potential ligand can be assessed by its ability to specifically block a mixed lymphocyte reaction (MLR) at concentrations of less than about 200 $\mu$M.

B. COMPOUNDS OF THE INVENTION

The invention encompasses any compound that is susceptible to computational screening by programs such as DOCK3.5 and that inhibits CD4-dependent rosetting and/or a mixed lymphocyte reaction. The molecular weight of compounds that can be readily screened by such tests and is large enough to function as an inhibitor is between about 150 and about 500 daltons.

Based on the screening of the forty one compounds selected from 150,000 compounds of the Available Chemicals Directory, four were found to inhibit CD-4 dependent resetting at less than 100 $\mu$M. The compounds are: A) TJU101, 5-(4-chlorobenzylthio)-3-{[(4-chlorophenyl)-2-thiazolyl]methylthiomethyl}-4-methyl-1,2,4-triazole; B) TJU102, 4-(4-methoxy-phenyl)-1-[imidazo(2,1-B) benzothiazole; C) TJU103, N-(3-indoylmethylene)-isonicotinic hydrazone; and D) TJU104, N-(2,4-dichlorophenyl)-3-(1,2,4-triazol-1-ylmethyl)-1,2,4-triazole-5-carboxamide, the structures of which are given in FIGS. 1A–1D.

Each of the compounds of the invention can be used to suppress a CD4 T-cell mediated immune response in mice and humans having a medical condition that is ameliorated by the suppression of a CD4 T-cell mediated immune response. For example, autoimmune diseases such as giant cell arteritis, polyarteritis nodosa, rheumatoid arthritis, scleroderma, multiple sclerosis, and SLE can be treated by administration of compounds of the present invention to a subject having one such.

Additionally, the compounds of the invention can be administered to a subject who has received an allogeneic graft, e.g., bone marrow, kidney or pancreas. The rejection of the graft can thereby be avoided. The compounds of the invention can be used in conjunction with immunosuppressive agents, well known to those skilled in the art. Compounds of the invention can be advantageously administered to a patient either prior to transplantation or later. Compounds of the present invention can be administered to patients suffering from graft versus host disease to inhibit the disease.

The compounds of the invention are shown to be effective to inhibit immune responses by the results of three assays: inhibition murine class II MHC disparate allograft rejection; inhibition of graft-versus-host disease, and the amelioration of murine EAE.

The effective amount of compound needed to treat a subject may be routinely determined through procedures well known to those skilled in the art which address such parameters as biological half-life, bioavailability, and toxicity. Such determination is well within the capability of those skilled in the art, especially in light of the detailed disclosure provided herein. For example, from the data presented in Examples 3–6, it is demonstrated that the administration of a single 50 µg dose of the compounds TJU101–104 is effective in ameliorating EAE in a mouse and/or significantly prolonging the median survival time of the allografts of C57Bl/6 mice challenged with C57Bl/6. H-$2^{bm12}$ tail skin grafts; that 0.1 mg doses of TJU103 compound administered i.v. on days 0, 3, and 6 post-transplant, is effective in prolonging median survival time of (B6×CBA)$F_1$ irradiated recipient mice transplanted with haploidentical (B6×DBA/2)$F_1$ T cell-depleted bone marrow and $CD4^+$ T cells; and that a 0.1 mg dose of the TJU103 compound, when administered i.v. 3 hours before transplantation, is effective in prolonging the median survival time of the allografts of B6 mice challenged with bm12 tail skin grafts.

The present invention provides pharmaceutical compositions that comprise the compounds of the invention and pharmaceutically acceptable carriers or diluents.

For parenteral administration, the compounds of the invention can be, for example, formulated as a solution, suspension, or lyophilized powder in association with a pharmaceutically acceptable parenteral vehicle. Examples of such vehicles are water, saline, Ringer's solution, dextrose solution, and 5% human serum albumin. The vehicle or lyophilized powder may contain additives that maintain isotonicity (e.g., sodium chloride, mannitol) and chemical stability (e.g., buffers and preservatives). For example, a parenteral composition suitable for administration by injection is prepared by dissolving 1.5% by weight of active ingredient in 0.9% sodium chloride solution. The formulation can be sterilized by any commonly used technique.

The pharmaceutical compositions according to the invention may be administered as a single dose or in multiple doses. The pharmaceutical compositions of the present invention may be administered either as individual therapeutic agents or in combination with each other or with other therapeutic agents. The treatments of the present invention may be combined with conventional therapies, which may be administered sequentially or simultaneously.

The pharmaceutical compositions of the present invention may be administered by any means that enables the active agent to reach the targeted cells. Because compounds of the invention may be subject to being digested when administered orally, parenteral administration, i.e., intravenous, subcutaneous or intramuscular, would ordinarily be used to optimize absorption. Intravenous administration may be accomplished with the aid of an infusion pump. Alternatively, the compounds of the invention can be formulated as aerosol medicaments for intranasal inhalation or topical administration.

The dosage administered varies depending upon factors such as: pharmacodynamic characteristics; its mode and route of administration; age, health, and weight of the recipient; nature and extent of symptoms; kind of concurrent treatment; and frequency of treatment. Usually, the dosage of the compound of the invention can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily, 8 to 800 milligrams are administered to an individual per day in divided doses 1 to 6 times a day or in sustained release form is effective to obtain desired results.

EXAMPLES

Example 1

Results of DOCK3.5

The GFCC'C" pocket is defined by residues 26–46 and 80–97 of human CD4 according to the atomic coordinates as published in Wang, J., et al., 1990, Nature 348, 411–418. The DOCK3.5 algorithm ranked the 150,000 compounds contained in the Available Chemicals Directory (Molecular Design Limited, San Leanardo, Calif.) according to their shape complementarity to the GFCC'C" pocket; the compound ranked 1 having the highest (most stable) complementarity score. The control parameters for DOCK3.5 that were used are given in Table 2.

Forty one compounds were selected for testing, of which 37 had shape complementarity ranks of better than 1000. Four of the 41 were found to inhibit CD4-class II MHC binding, see FIG. 2. The molecular weight (in daltons) and complementarity rank of each of these compounds is given in Table 1 below.

TABLE 1

SELECTED COMPOUNDS FOUND TO INHIBIT
CD4-class II MHC BINDING

| COMPOUND | MOLECULAR WEIGHT | DOCK3.5 Complementarity Score (RANK/150,000) |
|---|---|---|
| TJU101 | 493.5 | 233.0 (6) |
| TJU102 | 361.26 | 206.0 (33) |
| TJU103 | 264.29 | 180.0 (271) |
| TJU104 | 338.16 | 176.0 (372) |

The validity of the DOCK3.5 algorithm was verified by the observation that each of the effective compounds had a shape complementarity rank of better than 400 and two of the four had a rank of better than 40.

TABLE 2

DOCK3.5 PARAMETER FILE

MATCHING

| | |
|---|---|
| distance tolerance | 1.5 |
| nodes maximum | 10 |
| nodes minimum | 5 |
| ligand binsize | 0.4 |
| ligand overlap | 0.1 |
| receptor binsize | 0.4 |
| receptor overlap | 0.1 |
| bump maximum | 2 |
| focus cycles | 0 |

TABLE 2-continued

DOCK3.5 PARAMETER FILE

| mirror ligands | yes |
|---|---|
| SEARCH MODE | |
| ratio minimum | 0.2 |
| atom minimum | 6 |
| atom maximum | 120 |
| restart | no |
| number save | 1000 |
| normalize save | 0 |
| molecules maximum | 180000 |
| restart interval | 100 |
| initial skip | 0 |
| MINIMIZATION | |
| minimize | yes |
| check degeneracy | no |
| degeneracy wobble | 0 |
| degenerate save interval | 25 |
| check degenerate children | no |
| simplex iterations | 500 |
| simplex convergence | 0.2 |
| simplex restart | 1.0 |
| simplex initial translation | 1.0 |
| simplex initial rotation | 0.5 |

Example 2

Inhibition of CD4/Class II MHC Interactions

The sequence of human CD4 CDNA is given in Maddon, P. J. et al., 1985, CELL 42:93–104, which sequence is hereby incorporated by reference in its entirety. Maddon et al. refers to human CD4 as "T4." The plasmid T4-pMV7, containing the human CD4 cDNA is available from the AIDS Research and Reference Reagent Program, Division of AIDS, NIAID, NIH (McKesson BioServices, Rockville, Md.). The 3.0 Kb Eco R1 fragment of T4-pMV7 contains the 1.5 Kb CD4 CDNA.

For transfection of COS-7 cells, a CD4-expression plasmid T4-pcDNA3, was constructed by subcloning the 3.0 Kb Eco R1 fragment of T4-pMV7 into the EcoRI site of the mammalian expression vector pcDNA3 (INVITROGEN). Transfection was accomplished by DOSPER liposomal transfection reagent (BOEHRINGER MANNHEIM), by the following modification of the manufacturer's protocol.

1. In a six-well or 35 mm tissue culture plate, seed ~5×10$^4$ cells per well in 2 ml DEME containing 10% FCS (fetal calf sera, GIBCO) and nonessential amino acids.
2. Incubate the cells at 37° C., 5% $CO_2$ in a cell culture incubate until the cells are 70–80% confluent. This usually takes 18–24 h.
3. Prepare a DOSPER/DNA mixture:
    Solution A: dilute 2 μg T4 -pcDNA3 recombinant plasmid DNA with 20 mM HBS (Hepes-buffered saline, GIBCO) to a final volume of 50 μl.
    Solution B: dilute 6 μl DOSPER with 20 mM HBS to a final volume of 50 μl.
    Combine solution A and B, mix gently and incubate at room temperature for 15~30 min to allow the DOSPER/DNA complex to form.
4. On the day of transfection, replace the culture medium shortly before adding the DOSPER/DNA mixture with 1 ml serum-free DMEM.
5. Without removing the culture medium previously added, dropwise add 100 μl of the DOSPER/DNA complex to the cultures. It was essential to add the DOSPER/DNA complex dropwise. To ensure uniform distribution, mix by gently rocking the culture plate.
6. Incubate for 6 h at 37° C., 5% $CO_2$ in a cell culture incubator.
7. Following incubation, add 1 ml DMEM with 20% FCS without removing the transfection mixture.
8. Replace the medium containing DOSPER/DNA mixture 24 h after transfection with 2 ml fresh DEME with 10% FCS.
9. Determine the CD4 expression levels as a measure of transfection efficiency by flow cytometry analysis. Usually between 30% and 40% of transfected COS-7 cells expressed human CD4 as defined by immunofluorescence binding assay for the interaction between CD4 and class II MHC proteins in the presence of organic chemicals by rosette formation: Raji B cells 10$^7$ in 1 ml of RPMI medium with 10% FCS and 200 mM glutamine were added to each well 48 h post-transfection and incubated with transfected COS-7 cells in the presence of the test compound (individually 200 μM) at 37° C. for 1 h. Following incubation, wells were washed five or six times by dropping RPMI medium with FCS into wells. Rosette formation between Raji cells and transfected COS-7 cells was scored microscopically at 100-fold magnification. The number of rosette containing more than five Raji cells was counted in 10 random optical fields in each individual well; 300–400 rosettes per well were counted as the positive control for rosette formation without any inhibition in the absence of any chemicals. The inhibition activity for rosette formation for each chemical was determined by the ratio of the number of rosettes obtained in the presence of this chemical to the number of rosettes in the positive control. COS-7 cells transfected with pcDNA3 vector alone served as negative controls for rosette formation. No rosettes should be observed in the negative control wells.

The results of testing compounds TJU101–104 are presented in FIG. 2, which shows greater than 40% inhibition at 100 μM compound.

Example 3

EAE inhibition in vivo

The lead organic compounds were tested for in vivo immunosuppressive activity in murine EAE, an animal model for multiple sclerosis. An acute form of EAE was induced in SJL mice by subcutaneous challenge with proteolipid (PLP) epitope, MacRae, B. L., et al., 1995, J. Neuroimmunol. 60:17–28, (100 μg in 0.15 ml PBS emulsified in an equal volume of Complete Freund's Adjuvant) on days 0 and 7. Pertussis (Michigan Biological Products, Lansing Mich.) was administered 30 min after antigen injection on day 7 (0.25 ml containing 5×10$^9$ inactivated organisms, i.v.). Clinical symptoms of EAE were evaluated based on a 0–5 scale of ascending severity of symptoms, as previously described. Korngold, R., et al., 1986, Immunogenetics 24:309–315. The organic compounds were administered by a single i.v. injection of 50 μg of the compound in 0.25% DMSO (the compounds were not soluble in water alone) on day 12 post-challenge. The control injection of 0.25% DMSO alone showed that it had no effect on EAE in mice.

The results, shown in FIG. 3, demonstrated that all compounds appeared to reduce the severity of the disease and that two of the four compounds, TJU103 and TJU104, had a statistically significant effect (p<0.05).

Example 4
Effect of Compounds on Class II MHC Disparate Skin Graft Rejection

The lead organic compounds were tested for inhibition of CD4+ T cell-mediated skin allograft rejection using the MHC class II disparate model of C57B1/6 mice challenged with C57B1/6.H-$2^{bm12}$ tail skin. Following a modified method of Bailey and Usama (1960, Transplant. Bull. 7:424–425), donor tail skin grafts (0.25 cm×0.5 cm) were transplanted onto the ventral side of the tail of the recipient mouse, covered with a glass tube and held into position with short strips of adhesive tape for 2 days. The tubes were removed and the grafts monitored every other day for up to 80 days. Surviving grafts exhibited hair growth and full pigmentation. Syngeneic grafts were also transplanted as negative controls for rejection. Median survival times (MST) were calculated and statistical comparisons were performed by Wilcoxin signed-rank non-parametric analysis utilizing SYSTAT 5.2 software.

The compounds were injected 3 hours before transplantation at a dosage of 50 μg in 0.2 ml 0.25% DMSO. Each of the four compounds, so administered, was found to significantly prolong the median survival time of the allografts, in comparison to the untreated control mice ($p \geq 0.05$) (FIG. 4). Each group contained 4 animals except the TJU102 group, which contained 5 animals.

Example 5
Effect of TJU103 on the Development of Graft-Versus-Host Disease

The lead organic compound TJU103 (N-(3-indoylmethylene)-isonicotinic hydrazone) was tested for in vivo inhibition of CD4+ T cell-mediated graft-versus-host disease lethality. (B6×CBA)$F_1$ irradiated recipient mice were transplanted by i.v. injection with haploidentical (B6× DBA/2)$F_1$ T cell-depleted bone marrow (ATBM) and CD4+ T cells (3×10$^6$), which induces lethal graft-versus-host disease (GVHD). TJU103 was administered by i.v. injections at a dose of 100 μg in 0.5% DMSO on days 0, 3, and 6 post-transplant. The control injection of 0.5% DMSO alone showed that it had no effect upon survival of (B6×CBA)$F_1$ irradiated recipient mice transplanted with haploidentical (B6×DBA/2)$F_1$ T cell-depleted bone marrow and CD4+ T cells. Median survival times were calculated and statistical comparisons were performed by Wilcoxin signed-rank non-parametric analysis using SYSTAT 5.2 software.

The results, shown in FIG. 5, demonstrated that TJU103 significantly prolongs the median survival time of (B6× CBA)$F_1$ irradiated recipients transplanted with haploidentical (B6×DBA/2)$F_1$ T-cell depleted bone marrow and CD4+ T cells in comparison to the untreated control mice ($p<0.001$). Each group contained 15 animals except the DMSO group, which contained 10 animals.

Example 6
Effect of TJU103 on Skin Allograft Survival in the CD4+ T Cell-Mediated B6 anti-bm12 Response The lead organic compound TJU103 (N-(3-indoylmethylene)-isonicotinic hydrazone) was tested for inhibition of CD4+ T cell-mediated skin allograft rejection using the CD4+ T cell-mediated B6 anti-bm12 response. A single i.v. injection of 100 μg of TJU103 in 0.5% DMSO, was administered into B6 recipient mice 3 hours before transplantation of MHC class II-disparate bm12 tail skin allografts following a modified method of Bailey and Usama (1960 Transplant. Bull. 7:424–425). A group of mice were treated with anti-CD4 monoclonal antibody (GK1.5) as a negative control. Median survival times were calculated and statistical comparisons were performed by Wilcoxin signed-rank non-parametric analysis using SYSTAT 5.2 software.

The results shown in FIG. 6 demonstrated that TJU103, so administered, prolongs survival time of the allografts compared to mice treated only with 0.5% DMSO diluent. The control treatment with anti-CD4 monoclonal antibody (GK1.5) totally depletes recipient CD4+ T cells and also leads to allograft survival. Each group contained 5 animals.

Example 7
Effect of TJU103 on Skin Allograft Survival in the CD8+ T Cell-Mediated B6 anti-bm1 Response The lead organic compound TJU103 (N-(3-indoylmethylene)-isonicotinic hydrazone) was tested for inhibition of CD8+ T-cell mediated allograft survival using the CD8+ T cell-mediated B6 anti-bm1 response. A single i.v. injection of 100 μg of TJU103 in 0.5% DMSO was administered into B6 recipient mice 3 hours before transplantation of MHC class I-disparate bm1 tail skin allografts following a modified method of Bailey and Usama (1960, Transplant Bull. 7:424 425). A group of mice were treated with anti-CD8 monoclonal antibody (2.43) as a negative control. Median survival times were calculated and statistical comparisons were performed by Wilcoxin signed-rank non-parametric analysis using SYSTAT 5.2 software.

The results shown in FIG. 7 demonstrated that TJU103, so administered, does not prolong survival time of the allografts compared to mice treated only with 0.5% DMSO diluent. The control treatment with anti-CD8 monoclonal antibody (2.43) totally depletes recipient CD8+ T cells and leads to allograft survival. The combined results support the hypothesis that TJU103 is specific and only effective upon CD4+ T cell-mediated responses. Each group contained 5 animals.

The present invention is not to be limited in scope by the specific embodiments described which are intended as single illustrations of individual aspects of the invention, and functionally equivalent methods and components are within the scope of the invention. Indeed, various modifications of the invention in addition to those shown and described herein will become apparent to those skilled in the art from the foregoing description and accompanying drawings. Such modifications are intended to fall within the scope of the appended claims.

We claim:

1. A method of suppressing a human, CD4 T-cell immune response comprising administering to a subject having a medical condition that is ameliorated by the suppression of a CD4 T-cell mediated immune response, an effective amount of an active compound having a molecular weight of between 500 daltons and about 100 daltons, which compound, at a concentration of at most 100 μM:
   a) inhibits greater than 40% of the binding of human CD4-expressing, CD4-transfected COS cells to Raji cells; and
   b) causes a less than 20% decrease in the growth of EB-transformed lymphoblastoid cells and IL-2-dependent HT-2 cells.

2. The method of claim 1, wherein the molecular weight of the active compound greater than 250 daltons.

3. The method of claim 1, wherein the DOCK3.5 complementarity score of the active compound and the GFCC'C" pocket of the CD4 is at least 176.0.

4. The method of claim 3, wherein the complementarity score is between 233.0 and 176.0.

5. The method of claim 1, wherein the active compound is found in the Available Chemicals Directory.

6. The method of claim 1, wherein the compound:
 a) at a concentration of at most 100 μM causes less than a 20% decrease in the response of human peripheral blood lymphocytes to lipopolysaccharide; and
 b) delays the rejection of C57B1/6.H-$2^{bm12}$ skin grafts by C57B1/6 mice when given in a dose of 50 μg, 3 hours prior to engraftment, at least as long as a dose of 50 μg of 4-(4-methoxy-phenyl)-1-imidazo(2,1-B) benzothiazole, given 3 hours prior to engraftment, delays the rejection of C57B1/6.H-$2^{bm12}$ skin grafts by C57B1/6 control mice.

7. The method of claim 6, wherein the molecular weight of the active compound is greater than 250 daltons.

8. The method of claim 6, wherein the DOCK3.5 complementarity score of the active compound and the GFCC'C" pocket of the CD4 is at least 176.0.

9. The method of claim 8, wherein the complementarity score is between 233.0 and 176.0.

10. The method of claim 1, wherein the medical condition is related to an allograft.

11. The method of claim 1, wherein the medical condition is multiple sclerosis.

12. The method of claim 1, wherein the medical condition is an autoimmune disease.

13. The method of claim 12, wherein the autoimmune disease is selected from the group consisting of giant cell arteritis, polyarteritis nodosa, rheumatoid arthritis and scleroderma.

14. The method of claim 1, wherein the medical condition is graft-versus-host disease.

15. A method of suppressing a human, CD4 T-cell immune response comprising administering to a subject having a medical condition that is ameliorated by the suppression of a CD4 T-cell mediated immune response, an effective amount of a compound selected from the group consisting of 5-(4-chlorobenzylthio)-3-{[(4-chlorophenyl)-2-thiazolyl]methylthiomethyl}-4-methyl-1,2,4-triazole; 4-(4-methoxy-phenyl)-1-imidazo(2,1-B)benzothiazole; N-(3-indoylmethylene)-isonicotinic hydrazone; and N-(2,4-dichlorophenyl)-3-(1,2,4-triazol-1-ylmethyl)-1,2,4-triazole-5-carboxamide.

16. The method of claim 15, wherein the medical condition is related to an allograft.

17. The method of claim 15, wherein the medical condition is multiple sclerosis.

18. The method of claim 15, wherein the medical condition is an autoimmune disease.

19. The method of claim 18, wherein the autoimmune disease is selected from the group consisting of giant cell arteritis, polyarteritis nodosa, rheumatoid arthritis and scleroderma.

20. The method of claim 15, wherein the medical condition is graft-versus-host disease.

21. The method of claim 15, wherein the compound is N-(3-indoylmethylene)-isonicotinic hydrazone.

22. The method of claim 15, wherein the compound is 5-(4-chlorobenzylthio)-3-{[(4-chlorophenyl)-2-thiazolyl]methylthiomethyl}-4-methyl-1,2,4-triazole.

23. The method of claim 15, wherein the compound is 4-(4-methoxy-phenyl)-1-imidazo(2,1-B)benzothiazole.

24. The method of claim 15, wherein the compound is N-(3-indoylmethylene)-isonicotinic hydrazone.

25. The method of claim 15, wherein the compound is N-(2,4-dichlorophenyl)-3-(1,2,4-triazol-1-ylmethyl)-1,2,4-triazole-5-carboxamide.

26. The method of claim 1, wherein the compound is not 4-(4-methoxy-phenyl)-1-imidazo(2,1-B)benzothiazole.

27. The method of claim 1, wherein the compound is N-(3-indoylmethylene)-isonicotinic hydrazone.

* * * * *

UNITED STATES PATENT AND TRADEMARK OFFICE
CERTIFICATE OF CORRECTION

PATENT NO. : 6,127,387 Page 1 of 1
APPLICATION NO. : 08/987086
DATED : October 3, 2000
INVENTOR(S) : Ziwei Huang et al.

It is certified that error appears in the above-identified patent and that said Letters Patent is hereby corrected as shown below:

Column 14, Line 26, Claim 24: Please change "15" to --6--.

Signed and Sealed this

Seventeenth Day of April, 2007

JON W. DUDAS
*Director of the United States Patent and Trademark Office*